United States Patent
Bantia

(10) Patent No.: US 9,452,217 B2
(45) Date of Patent: Sep. 27, 2016

(54) METHODS FOR POTENTIATING IMMUNE RESPONSE FOR THE TREATMENT OF INFECTIOUS DISEASES AND CANCER

(71) Applicant: Shanta Bantia, Birmingham, AL (US)

(72) Inventor: Shanta Bantia, Birmingham, AL (US)

(73) Assignee: Nitor Therapeutics, Birmingham, AL (US)

( * ) Notice: Subject to any disclaimer, the term of this patent is extended or adjusted under 35 U.S.C. 154(b) by 0 days.

(21) Appl. No.: 14/309,069

(22) Filed: Jun. 19, 2014

(65) Prior Publication Data

US 2014/0378482 A1 Dec. 25, 2014

Related U.S. Application Data

(60) Provisional application No. 61/838,252, filed on Jun. 22, 2013, provisional application No. 61/887,625, filed on Oct. 7, 2013, provisional application No. 61/934,094, filed on Jan. 31, 2014.

(51) Int. Cl.

| | | |
|---|---|---|
| A61K 31/70 | (2006.01) | |
| A61K 47/22 | (2006.01) | |
| A61K 39/00 | (2006.01) | |
| A61K 31/519 | (2006.01) | |
| A61K 45/06 | (2006.01) | |
| A61K 39/08 | (2006.01) | |
| A61K 39/39 | (2006.01) | |
| A61K 31/7064 | (2006.01) | |

(52) U.S. Cl.
CPC ............ *A61K 47/22* (2013.01); *A61K 31/519* (2013.01); *A61K 39/00* (2013.01); *A61K 39/08* (2013.01); *A61K 39/39* (2013.01); *A61K 45/06* (2013.01); *A61K 31/7064* (2013.01); *A61K 2039/55511* (2013.01)

(58) Field of Classification Search
CPC ........................ A61K 31/519; A61K 31/7064
USPC ........................................................ 514/45
See application file for complete search history.

(56) References Cited

U.S. PATENT DOCUMENTS

| | | |
|---|---|---|
| 4,938,949 A | 7/1990 | Borch et al. |
| 4,985,433 A | 1/1991 | Secrist, III et al. |
| 4,985,434 A | 1/1991 | Secrist, III et al. |
| 5,008,265 A | 4/1991 | Secrist, III et al. |
| 5,008,270 A | 4/1991 | Secrist, III et al. |
| 5,565,463 A | 10/1996 | Secrist, III et al. |
| 5,721,240 A | 2/1998 | Secrist, III et al. |
| 5,891,864 A | 4/1999 | Han et al. |
| 5,985,848 A | 11/1999 | Furneaux et al. |
| 6,066,722 A | 5/2000 | Furneaux et al. |
| 7,109,331 B2 | 9/2006 | Furneaux et al. |
| 7,390,890 B2 | 6/2008 | Furneaux et al. |
| 7,427,624 B2 | 9/2008 | Chen et al. |
| 7,553,839 B2 | 6/2009 | Evans et al. |
| 8,173,662 B2 | 5/2012 | Evans et al. |
| 8,283,345 B2 | 10/2012 | Evans et al. |
| 2001/0053784 A1 | 12/2001 | Morris, Jr. et al. |
| 2003/0114466 A1 | 6/2003 | Bantia et al. |
| 2005/0250728 A1* | 11/2005 | Bantia ............ A61K 31/7064 514/45 |
| 2009/0239885 A1 | 9/2009 | Evans et al. |
| 2011/0038858 A1 | 2/2011 | Bantia et al. |
| 2011/0130412 A1 | 6/2011 | Clinch et al. |

FOREIGN PATENT DOCUMENTS

| | | |
|---|---|---|
| WO | 2005025583 | 3/2005 |
| WO | 2008030119 | 3/2008 |

OTHER PUBLICATIONS

International Search Report and Written Opinion of corresponding PCT Application No. PCT/US2014/043141 mailed Oct. 10, 2014.

\* cited by examiner

*Primary Examiner* — Kevin E Weddington

(74) *Attorney, Agent, or Firm* — Dinsmore & Shohl LLP

(57) ABSTRACT

Compositions and methods including at least one PNP inhibitor or at least one PNP inhibitor in combination with one or more agents identified as endogenous adjuvants useful in the treatment of pathogen infection and cancer are disclosed. The compositions may be formulated as pharmaceutical dosage forms and components may be assembled as kits. Methods for increasing levels of endogenous adjuvants to enhance an immune response and to potentiate/augment antiviral, antibacterial or anticancer effects of therapeutic agents are also disclosed.

9 Claims, 10 Drawing Sheets

* p ≤ 0.003; ** ≤ 0.0001 vs Vehicle

METHODS FOR POTENTIATING IMMUNE RESPONSE FOR THE TREATMENT OF INFECTIOUS DISEASES AND CANCER

RELATED APPLICATIONS

This application claims the benefit of U.S. provisional application Ser. No. 61/838,252 filed on Jun. 22, 2013, U.S. Provisional Ser. No. 61/887,625 filed on Oct. 7, 2013, and U.S. Provisional Ser. No. 61/934,094 filed Jan. 31, 2014, the entire disclosures of which are incorporated herein by this reference.

TECHNICAL FIELD

The invention relates to pharmaceutical compositions comprising certain Purine Nucleoside Phosphorylase (PNP) inhibitors and/or agents identified as endogenous adjuvants, which provide antiviral, antibacterial and anticancer effects and which provide an immunopotentiating effect when administered in conjunction with antiviral, antibacterial or anticancer agents. The invention also relates to methods of treating diseases, enhancing an immune response, and augmenting antiviral, antibacterial and anticancer therapies employing the inventive compositions.

BACKGROUND

In the past, antiviral and antibacterial research has focused mainly on viral and bacterial targets. Due to continued growth of drug resistant organisms the search for effective and differentiated antiviral and antibacterial therapies continues. Development of immune-potentiating agent is one of the strategies being pursued to identify new anti-infective agents. An adjuvant is an agent administered to potentiate the immune response to an antigen and/or modulate it towards a desired immune response. An endogenous adjuvant is a compound or molecule naturally occurring within the cell or tissue that likewise enhances an immune response by stimulating innate immunity, thus possessing the capacity to potentiate an effect of some triggering event or agent. Endogenous adjuvants play a central role in alerting the immune system to potential danger and promote response to infection, transplantation, tumor, and autoimmunity.

Some endogenous adjuvants are known to promote CD8+ T-cell immune responses which are important in combating infections associated with pathogens, such as viruses and bacteria as well as controlling the tumor growth (Rock et al, in *Springer Seminars in Immunopathology* (2005) 26:231-246).

PNP deficient patients have demonstrated significantly high levels of plasma nucleosides, inosine, deoxyinosine, guanosine and deoxyguanosine compared to normal healthy subjects (Markert in *Immunodeficiency Review* (1991) 3:45-81) and also elevated levels of erythrocyte deoxyguanosine triphosphate (dGTP) and nicotinamide adenine dinucleotide (NAD). Plasma deoxyguanosine (only nucleoside measured in the clinic) and intracellular dGTP was elevated in patients treated with PNP inhibitor (Bantia and Kilpatrick in *Current Opinions in Drug Discovery & Development* (2004) 7: 243-247). Deoxyguanosine was also elevated in mouse plasma after treatment with PNP inhibitor (Bantia et al. in *International Immuno-pharmacology* (2001) 1:1199-1210 and (2010) 10:784-790).

A major source of nucleoside pools comes from the breakdown of RNA and DNA during normal cell turnover, cellular injury or cell death due to infection. Normally the nucleosides deoxyguanosine, inosine, deoxyinosine, and guanosine are present at very low levels in the plasma because PNP is an extremely efficient catalyst and rapidly breaks down inosine and deoxyinosine to hypoxanthine, and, guanosine and deoxyguanosine to guanine and sugar 1-phosphate. In the presence of PNP inhibitor or due to a PNP deficiency, however, these nucleosides, guanosine, inosine, deoxyinosine, and deoxyguanosine, are elevated.

Guanosine analogs like isatoribine (7-thia, 8-oxoguanosine), loxorabine (7-allyl, 8-oxo guanosine) and others have shown to be immuno-potentiators and have demonstrated antiviral, antibacterial and anticancer effects in animal models (Smee et al. in *Antimicrobial Agents and Chemotherapy* (September 1989) 1487-1492; Stewart et al. in *J. Interferon Cytokine Research* (2012) 32(1):46-51; also in *Poult Science* (2012) 91(4):1038-1042; Pope et al. in *Cell Immunol.* (1995) 162(2):333-339).

ANA773, an oral pro-drug of isatoribine, and has demonstrated induction of endogenous interferon-a (IFN-a) of multiple subtypes in healthy volunteers. ANA773 in clinical trials of chronically HCV infected patients demonstrated dose dependent reduction in HCV RNA (Bergmann et al. in *Aliment Pharmacol Ther* (2011) 34:443-453; International patent number WO2005025583A2).

In-vitro studies with these guanosine analogs have shown activation of immune cells like dendritic, natural killer cell to produce ifn-gamma which is mediated through Toll-Like Receptor 7 (TLR7). Toll-like receptors (TLRs) have been established as a family of pathogen recognition receptors (PRRs) that initiate the innate immune response. In addition to TLR.s there are other PRRs like retinoic acid inducible gene I (RIGI) like receptors (RLR), nucleotide binding oligomerization domain (NOD)-like receptors (NLR) as well as c-type lectin receptors (CLR). Stimulation of TLRs and PRRs directly or indirectly causes the release of multiple cytokines including type 1 and type 2 interferons, the induction of pathways and enzymes that destroy intracellular pathogens, the activation of a variety of cellular responses, and the priming of the adaptive response by activating immature dendritic cells and inducing their differentiation into professional antigen-presenting cells. At least eleven different TLR genes have been identified in humans. Through stimulation of innate immunity by activating TLR, isatoribine and other guanosine analogs does prevent or reverse otherwise lethal viral infections in various acute infection models in mice.

The Inosine analog methyl inosine monophosphate has also shown immune enhancing effects and demonstrated antiviral and antibacterial effects (Mishin et al. in *Antiviral Research* (2006) 71:64-68).

In addition to the accumulation of nucleosides in the presence of PNP inhibitor, deoxyguanosine is converted to dGTP in lymphocytes and erythrocytes and dGTP could stimulate the immune system through activation of PRRs in the presence of an antigen similar to what has been observed with ATP. Although the mechanism is not clear PNP deficient patients also demonstrate increase in the nucleotide, NAD levels. NAD may also serve as danger signal and activate the immune system (Haag et. Al., Purinergic Signalling (2007) 3:71-81)

Based on the role of PNP in purine catabolism, the present investigators hypothesize that inhibiting PNP may elevate nucleosides, inosine, deoxyinosine, guanosine and deoxyguanosine levels and nucleotides, NAD and dGTP in a subject as demonstrated in PNP deficient patients and PNP deficient mice (FIG. 1). Humans and mice treated with PNP inhibitor demonstrate significant increase in levels of plasma deoxyguanosine, the only nucleoside that has been measured.

Clearly it would be beneficial to provide methods for treating diseases which exploit the natural endogenous adjuvant response. Controlling levels of endogenous adjuvants provides a novel means to augment antiviral, antibacterial and anticancer treatments. Further, identification of endogenous adjuvants triggered in response to certain pathogens could provide novel exogenous adjuvants which may be administered to enhance an immune response and/or to potentiate the therapeutic efficacy of other antiviral, antibacterial and anticancer treatments.

SUMMARY

Accordingly, it is an object of the instant invention to provide compositions and methods which exploit the endogenous adjuvant response to directly treat disease or to enhance the therapeutic effects of antiviral, antibacterial and anticancer agents. In a first aspect, the present disclosure provides an article of manufacture, and methods and composition for increasing the nucleosides, inosine, deoxyinosine, guanosine and deoxyguanosine, and the nucleotides, NAD and dGTP levels in a subject.

The present disclosure describes compositions and methods for inhibiting PNP and for effectuating an increase in inosine, deoxyinosine, guanosine, deoxyguanosine, NAD and dGTP pools in a subject. These endogenous substances behave as endogenous adjuvants and can act as immune-enhancers in the presence of foreign pathogens and tumor antigens translating into antiviral, antibacterial and anticancer effects. Such compositions and methods were not previously appreciated in the art.

The present disclosure further describes compositions, kits and methods useful for inhibiting PNP in combination with one or more exogenous nucleosides including inosine, deoxyinosine, guanosine, and deoxyguanosine, and the exogenous nucleotide NAD and dGTP, individually or in combination, which can act as immune-enhancers in the presence of foreign pathogens and tumor antigens translating into antiviral, antibacterial and anticancer effects. Such compositions and methods were not previously appreciated in the art.

One embodiment provides methods of treating a disease or condition in which it is desirable to increase an amount of at least one endogenous adjuvant, the method comprising administering a pharmaceutically effective amount of a purine nucleoside phosphorylase (PNP) inhibitor to a subject requiring treatment.

According to another embodiment, methods for enhancing a potentiating effect of at least one endogenous adjuvant in a subject being treated with an anti-cancer, anti-viral or anti-bacterial agent, the method comprising administering a purine nucleoside phosphorylase (PNP) inhibitor to the subject in conjunction with the agent are provided. The methods may further comprise administering an agent identified as an endogenous adjuvant simultaneous or subsequent to administration of the PNP inhibitor.

Methods for treating diseases or conditions in which it is desirable to increase an amount of at least one endogenous adjuvant are also provided. According to one embodiment, the methods comprise administering a pharmaceutically effective amount of a composition comprising at least one purine nucleoside phosphorylase (PNP) inhibitor and at least one agent identified as an endogenous adjuvant to a subject requiring treatment.

According to other embodiments, compositions effective for enhancing an immune system response in a subject are provided. The compositions comprise at least one PNP inhibitor and at least one agent identified as an endogenous adjuvant. Compositions may be formulated as oral dosage forms, parenteral dosage form or topical dosage form and in specific embodiments the oral dosage form is formulated to provide delayed release of the PNP inhibitor relative to the agent identified as an endogenous adjuvant.

Kit embodiments are also disclosed. In some embodiments the kits comprise a first dosage form and a second dosage form, the first dosage form comprising a PNP inhibitor and the second dosage form comprising at least one agent identified as an endogenous adjuvant.

These and other embodiments and aspects of the present invention will be expanded and clarified by reference to the Detailed Description set forth below.

DETAILED DESCRIPTION

TLRs play a critical role in the early innate immune response to invading pathogens by sensing microorganism and are involved in sensing endogenous danger signals. TLRs recognize highly conserved structural motifs known as pathogen-associated microbial patterns (PAMPs), which are exclusively expressed by microbial pathogens, or danger-associated molecular patterns (DAMPs) that are endogenous molecules released from necrotic or dying cells. Stimulation of TLRs by the corresponding PAMPs or DAMPs initiates signaling cascades leading to the activation of transcription factors, such as AP-1, NF-κB and interferon regulatory factors (IRFs). Signaling by TLRs result in a variety of cellular responses including the production of interferons (IFNs), pro-inflammatory cytokines and effector cytokines that direct the adaptive immune response.

PNP (sometimes referred to as PNPase) deficiency is known to result in an increase in levels of the substrates of the enzyme, including inosine, deoxyguanosine, deoxyinosine and guanosine. In addition to increases in specific nucleosides, PNP inhibition also leads to accumulation of intracellular dGTP and NAD (Markert in *Immunodeficiency Review* (1991) 3:45-81). The present investigators posit that these nucleosides and nucleotides NAD and dGTP can act as endogenous adjuvants similar to other purines known as putative endogenous adjuvants such as uric acid, ATP and adenosine and, therefore, can activate the immune system through TLRs and/or other PRRs in the presence of an appropriate antigen related to foreign pathogen or tumor cells translating into beneficial antiviral, antibacterial and anticancer effects.

Figure 1:
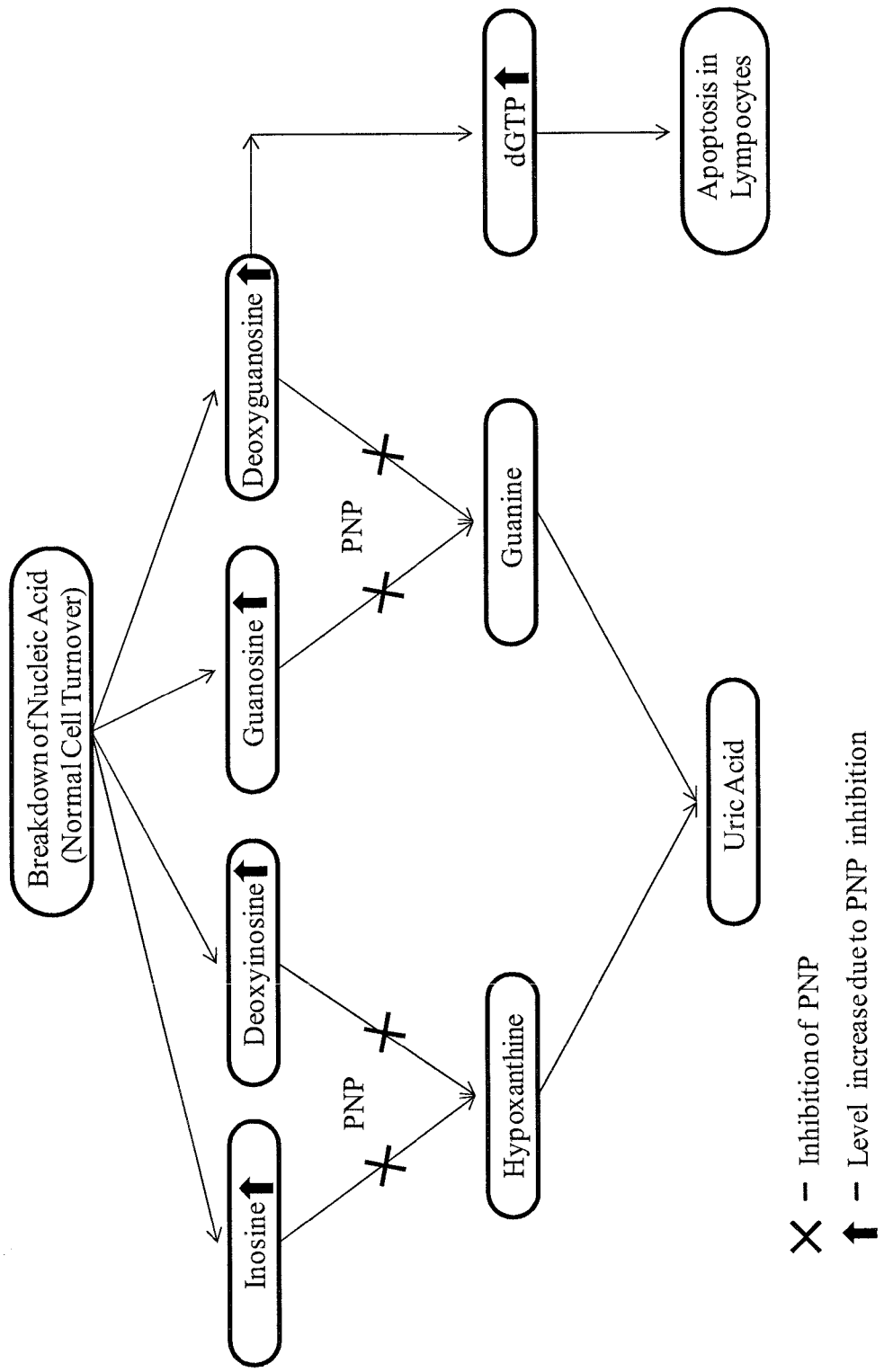
FIG. 1. Depicts a schematic illustration of the relationship between PNP inhibition and levels of inosine, deoxyinosine, guanosine, deoxyguanosine, and nucleotide dGTP levels.

FIG. 1 is a schematic presentation of the role of PNP in purine metabolism which illustrates the relationship between PNP inhibition and increases in inosine, deoxyinosine, guanosine, deoxyguanosine, and nucleotide dGTP levels.

PNP-deficient patients and PNP-deficient mice demonstrate high levels of these nucleosides and nucleotides, NAD and dGTP. Patients treated with PNP inhibitor or animals treated with PNP inhibitor show increases in plasma levels of deoxyguanosine. A major source of nucleoside pools comes from the breakdown of RNA and DNA during cellular injury or cell death. Normally, the nucleosides deoxyguanosine, inosine, deoxyinosine, and guanosine are present at very low or undetectable levels in the plasma because PNP rapidly breaks down inosine and deoxyinosine to hypoxanthine, and guanosine and deoxyguanosine to guanine and sugar 1-phosphate. In the presence of PNP inhibitor or PNP deficiency these nucleosides are elevated which could potentially act as endogenous adjuvant and activate the immune system.

The present investigators discerned, therefore, that increases in one or more of these PNP substrates and NAD and dGTP, due to inhibition of PNP could act as danger signal (endogenous adjuvant) and enhance the immune system in the presence of an appropriate antigen related to foreign pathogen or tumor cells translating into beneficial antiviral, antibacterial and anticancer effects.

Guanosine analogs like isatoribine (7-thia, 8-oxoguanosine), loxorabine (7-allyl, 8-oxo guanosine) have demonstrated immune-potentiating effects, in-vitro studies with some guanosine analogs have shown activation of immune cells, for example dendritic cells and natural killer cells to produce ifn-gamma which is mediated through Toll-Like Receptor 7 (TLR7).

Through stimulation of innate immunity by activating TLR, isatoribine and other guanosine analogs appear to prevent or reverse otherwise lethal viral infections in various acute infection models in mice. The present investigators therefore posit that by inhibiting PNP, guanosine and other nucleoside levels are elevated and may activate an innate immune response through TLRs and other PRRs like the guanosine analogs, isatoribine and loxoribine, translating into beneficial antiinfective and anticancer effects.

Embodiments of the present invention therefore provide methods for preventing and treating diseases which recognize and exploit the natural endogenous adjuvant response. Controlling/modulating the levels of endogenous adjuvants provide a novel means to enhance immunogenicity of an appropriate antigen related to foreign pathogen or tumor cells translating into beneficial antiviral, antibacterial and anticancer effects Further, identification of endogenous adjuvants triggered in response to certain pathogens could provide novel exogenous adjuvants which may be administered in conjunction with antiinfective and anticancer agents.

Aspects of the invention related to affirmatively inhibiting PNP to effectuate elevation of plasma inosine, deoxyinosine, guanosine, and deoxyguanosine levels and intracellular dGTP levels in a subject, as is observed in PNP deficient patients (FIG. 1).

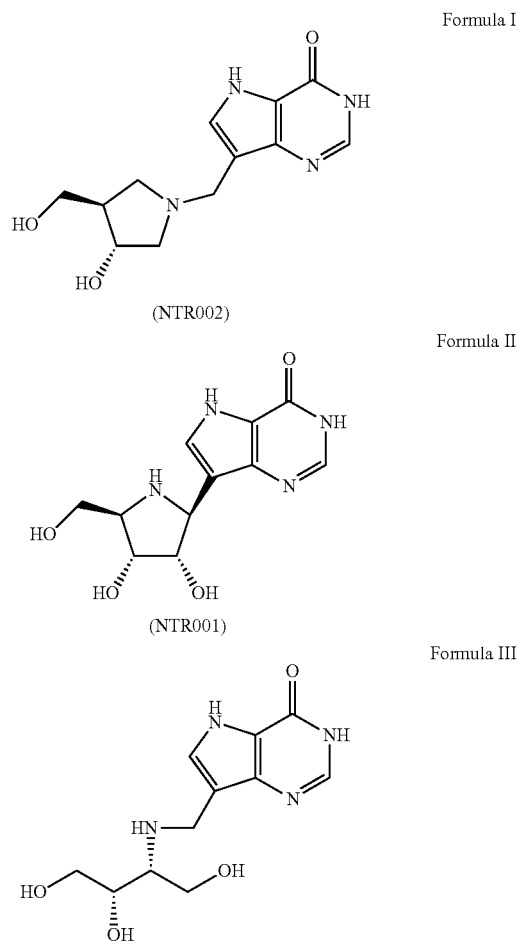

Formula I (NTR002)

Formula II (NTR001)

Formula III

Compounds depicted structurally by Formula I (NTR002, also known as Ulodesine 1,5-dihydro-7-[[(3R,4R)-3-hydroxy-4-(hydroxymethyl)pyrrolidin-1-yl]methyl]-4H-pyrrolo [3,2-d]pyrimidin-4-one), Formula II (NTR001, also known as Forodesine 7-[(2S,3S,4R,5R)-3,4-dihydroxy-5-(hydroxymethyl)-2-pyrrolidinyl]-1,5-dihydro-4H-pyrrolo [3,2-d]pyrimidin-4-one) and Formula III have been shown to inhibit PNP. Further, structurally similar compounds known as transition state analogs have been studied as PNP inhibitors (Evans et al. in *Organic Letters* (2003) 5:3639; Taylor et al. in *Journal of American Chemical Society* (2007) 129:6984; Evans et al. in *Journal of Medicinal Chemistry* (2003) 46:5271; Castilho et al. in *Bioorganic & Medicinal Chemistry* (2006) 14:516; Schramm et al. in *Journal of Biological Chemistry* (2007) 282:28297; and Bantia et al. in *International Immunopharmacology* (2010) 784 and (2001) 1:1199-1210; Kicska et al. in *Proceedings of National Academy of Sciences* (2001) 98:4593-4598). The disclosures of each of these references are hereby incorporated in the entirety by this citation. Non-limiting examples of PNP inhibitors include those disclosed in U.S. Pat. Nos. 4,985,433; 4,985,434, 5,008,265; 5,008,270; 5,565,463 7,427,624, 5,721,240, 5,985,848, 7,390,890 and the continuation patents that are referenced therein, 7,109,331, 8,283,345, 8,173,662 and 7,553,839, and International Patent Number WO2008/030119 and EP2395005, the disclosures of which are also incorporated herein in the entirety by this reference.

The term "PNP inhibitor" includes those compounds that inhibit PNP. Compositions having in-vitro inhibitory constant (Ki) values of less than about $5\times10^{-6}$ M, typically less than about $1\times10^{-7}$ M, and preferably less than $5\times10^{-8}$ M are preferred for in vivo use.

In one embodiment, the present disclosure provides methods and compositions for inhibition of PNP and increase in the nucleoside inosine, deoxyinosine, guanosine, and deoxyguanosine levels, and in the nucleotide NAD and dGTP levels. In an alternate embodiment, the present disclosure provides for methods and compositions useful for antiviral, antibacterial and anticancer effects by a PNP inhibitor related to elevated inosine, deoxyinosine, guanosine, and deoxyguanosine, and elevated NAD and dGTP levels, each of which individually or in combination can act as an endogenous adjuvant to stimulate the immune system in subjects.

In another embodiment, the present disclosure further provides for methods and compositions useful for antiviral, antibacterial and anticancer effects by administration of a combination of a PNP inhibitor with other antiviral, antibacterial and anticancer agents In yet another embodiment, the present disclosure further provides methods and compositions useful for antiviral, antibacterial and anticancer effects by administration of a combination of one or more PNP inhibitors and one or more agents identified as endogenous adjuvants selected from inosine, deoxyinosine, guanosine, deoxyguanosine, NAD and dGTP.

The present disclosure also provides articles of manufacture useful for increasing concentrations of one or more of inosine, deoxyinosine, guanosine, deoxyguanosine, NAD and dGTP in a subject. The present disclosure also provides articles of manufacture useful for providing antiviral, antibacterial and anticancer effects by increasing concentrations of inosine, deoxyinosine, guanosine, deoxyguanosine, NAD and/or dGTP in a subject in need of antiviral, antibacterial and/or anticancer effects. According to one specific embodiment, the article of manufacture comprises at least one reservoir containing a composition comprising one or more compounds structurally depicted by Formula I, Formula II, and Formula III, trivial variants thereof, PNP inhibitors listed in U.S. Pat. Nos. 5,985,848, 6,066,722 and 7,553,839, and international Patent Number WO2008/030119, and agents identified as endogenous adjuvants including but not limited to inosine, deoxyinosine, guanosine, deoxyguanosine, NAD and dGTP. The articles of manufacture may be packaged with instructions relating to indications for various disorders that the compositions are capable of treating.

Compounds of Formulas I, II and III are 9-deazahypoxanthine derivatives. Compounds of Formula I, II, III and related compounds are described in U.S. Pat. Nos. 5,985,848, 6,066,722 and 7,553,839 and International Patent Number WO2008/030119. In some embodiments of this disclosure, these compounds can exist as a pharmaceutically acceptable salt, In other embodiments these compounds can exist in a racemic equilibrium or as a specific tautomer. In yet other embodiments these compounds can exist as a solvate. In yet other embodiments these compounds can exist as a hydrate. In yet other embodiments these compounds can exist as a prodrug.

Furthermore, in the embodiments described above, the article of manufacture may contain a therapeutically effective amount of one or more compounds depicted by Formulas I, II, and III and related compounds such as those described in U.S. Pat. Nos. 5,985,848, 6,066,722 and 7,553,839 and International Patent Number WO2008/030119, The one or more compounds may also be provided in combination one or more of inosine, deoxyinosine, guanosine, deoxyguanosine, NAD and dGTP.

In other specific embodiments the article of manufacture may further comprise, consist essentially of, or consist of, one or more additional active agents in combination with one or more of the compounds of Formula I, II, III and related compounds such as those described in U.S. Pat. Nos. 5,985,848, 6,066,722 and 7,553,839, and in International Patent Number WO2008/030119. In more specific embodiments the combination may further include one or more of inosine, deoxyinosine, guanosine and deoxyguanosine, NAD and dGTP. Examples of active agents include but are not limited to analgesic agents, anti-inflammatory agents, anti-infective agents, anticancer agents, chemotherapeutic agents, agents that inhibit purine metabolism and other active agents know in the art.

Pharmaceutical Composition and Medicaments

Compounds may be administered as oral, parenteral, topical, or any other known method of administration in the literature and the formulations also may be prepared according to the requirements and the procedures reported in the literature. In specific embodiments compositions comprising the compounds of the invention are formulated in delay-release or extended-release dose forms. For example, a compound comprising a PNP inhibitor may be formulated in a delay release form such that if administered together with another agent such that the PNP inhibitor will be released after the other agent is released in the subject.

Methods of Treatment

One embodiment is directed to methods for increasing concentrations of inosine, deoxyinosine, guanosine and deoxyguanosine, NAD and dGTP in a subject, the method comprising administering to the subject a therapeutically effective amount of one or more compounds of Formula I, II and III, a trivial variant thereof, a pharmaceutically acceptable salt, tautomer, isomer, prodrug, solvate or hydrate thereof, and optionally a pharmaceutically acceptable carrier.

In another embodiment, the present disclosure provides for methods for enhancing the potency of endogenous adjuvant in a subject, the method comprising administering to the subject a therapeutically effective amount of compound of the formula I, II and III or a pharmaceutically acceptable salt, tautomer, isomer, prodrug, solvate or hydrate thereof, one or combination of the four nucleosides inosine, deoxyinosine, guanosine and deoxyguanosine, and nucleotides NAD and dGTP and an optional pharmaceutically acceptable carrier.

Dosages Administered

In one embodiment, useful dosages of the compound of the Formulas I, II and III, and related compounds described in U.S. Pat. Nos. 5,985,848, 6,066,722 and 7,553,839, and International Patent Number WO2008/030119, can be determined by comparing their in vitro activity, and in vivo activity in animal models. Methods for the extrapolation of effective dosages in mice, and other animals, to humans are known to the art; for example, see U.S. Pat. No. 4,938,949, the entire content of which is incorporated herein by reference.

It is known that PNP inhibition in humans over long term at certain doses leads to decreases in various lymphocyte subsets (Gomes et al. in *Blood ASH Annual Meeting Abstracts* (2008) 112:Abstract 2583). Hence, long term treatment with high doses of PNP inhibitor may have immunosuppressive effects. Surprisingly, the present investigators discovered that PNP inhibitors exhibit an immune-potentiating effect in the presence of an antigen if doses are selected to avoid significant impact on lymphocytes.

The magnitude of a prophylactic or therapeutic dose of PNP inhibitor or a pharmaceutically acceptable salt, solvate, hydrate, or stereoisomer thereof in the acute or chronic treatment or prevention of an infection or cancer will vary, with the nature and severity of the infection and the cancer and the route by which it is administered. The dose, and in some cases the dose frequency will also vary according to the infection and the cancer to be treated, the age, body weight and response of the individual patient. Suitable dosing regimens can be readily selected by those skilled in the art with due consideration of such factors.

The following Examples are set forth to illustrate certain aspects and features of the instant inventive subject matter and should not be construed as limiting the full scope as defined by the claims appended hereto. Example 1 described below demonstrate that guanosine, which is one of the nucleoside that is elevated when PNP is inhibited, activate TLR2 and TLR4. Activation of TLR2 and TLR4 results in immune potentiating effects as it leads to expression of transcription factors (like NF-kB ans IRF-3) resulting in expression of inflammatory cytokines and other cellular activation events. Examples 2, 3 and 4 demonstrate the immune potentiating activity of PNP inhibitor in in-vivo mouse models of cancer, infection and vaccine. For purposes of interpreting this disclosure, Formulas I, II and III include trivial variants thereof, the term "trivial" being with respect to pharmaceutical efficacy. NTR001 is depicted structurally as Formula II, and NTR002 is depicted structurally as Formula I.

EXAMPLE 1

Toll-Like Receptor (TLR) Ligand Screening: In-vitro Activity of the PNPi, Guanosine and Inosine on Seven Different Human TLRs (TLR2, 3, 4, 5, 7, 8 and 9) as a Potential Agonist TLRs play a critical role in the early innate immune response to invading pathogens by sensing microorganism and are involved in sensing endogenous danger signals. TLRs recognize highly conserved structural motifs known as pathogen-associated microbial patterns (PAMPs), which are exclusively expressed by microbial pathogens, or danger-associated molecular patterns (DAMPs) that are endogenous molecules released from necrotic or dying cells. Stimulation of TLRs by the corresponding PAMPs or DAMPs initiates signaling cascades leading to the activation of transcription factors, such as AP-1, NF-κB and interferon regulatory factors (IRFs). Signaling by TLRs result in a variety of cellular responses including the production of interferons (IFNs), pro-inflammatory cytokines and effector cytokines that direct the adaptive immune response. This Example investigates the potential TLR agonism of PNP inhibitors NTR001 (Foredesine set forth as Formula II), inosine and guanosine alone and in combination with respect to seven different human TLRs (TLR2, 3, 4, 5, 7, 8 and 9).

Method: TLR stimulation is tested by assessing NF-κB activation in HEK293 cells expressing a given TLR. The Secreted Embryonic Alkaline Phosphatase (SEAP) reporter is under the control of a promoter inducible by the transcription factor NF-κB. This reporter gene allows the monitoring of signaling through the TLR, based on the activation of NF-κB. The compounds are evaluated at one concentration and compared to control ligands. This step is performed in triplicate.

Figure 2:
FIG. 2. Activity of the NTR001, inosine and guanosine as single agent and in combination on seven different human TLRs (TLR2, 3, 4, 5, 7, 8 and 9) as a potential agonist FIG. 3. Serum tetanus toxoid antibody titers on day 38 in vehicle- and PNP inhibitors NTR001- and NTR002-treated mice groups in the tetanus toxoid mouse model.

Results: Guanosine (100 uM) exhibits a significant stimulatory effect on human TLR2 and TLR4, alone or in combination with article NTR001 (10 uM) and/or Inosine (100 uM). NTR001, Inosine, and NTR001+Inosine do not exhibit a stimulatory effect on human TLR2, 3, 4, 5, 7, 8 or 9. (FIG. 2)

Conclusion: Guanosine is an agonist of TLR2 and TLR4 receptors. Activation of TLR2 and TLR4 results in immune activation and hence treatment with a combination guanosine and PNPi (to prevent breakdown of guanosine) or PNPi alone (elevates guanosine in vivo) would be beneficial for the prevention and the treatment of cancer and infections.

EXAMPLE 2

This Example Evaluates PNPi as an Adjuvant in Tetanus Toxoid Vaccine Efficacy Study Background: Aluminium based mineral salts (Alum) have been used as adjuvants in licensed vaccines for many years. Although alum has been shown to be safe and effective in traditional vaccines where eliciting antibody response is necessary, it is a weak adjuvant for protein subunits, which is one of the major drawbacks. Another limitation of alum is that it fails to induce the Th1 response associated with the induction of interferon-gamma (interferon-g) and cytotoxic T lymphocytes (CTL). Natural control of infectious diseases such as HIV, malaria and tuberculosis that cause the most global mortality are either entirely or partially dependent on the generation of Th1-type immunity. This Example demonstrates that the PNP inhibitors NTR001 (Forodesine set forth structurally herein as Formula II) and NTR002 (Ulodesine set forth structurally herein as Formula I) enhance the potency of the tetanus toxoid vaccine by increasing the antibody titers, and in particular illustrates induction of Th1 responses associated with the induction of interferon-g.

Method: Tetanus toxoid (TT) was used to vaccinate mice thrice, two weeks apart. Mice were treated by oral administration of compounds NTR001 and NTR002 and serum was collected at various time points for antibody titer and interferon-g analysis. Mice in Groups 2-6 (Table 2) are vaccinated subcutaneously with 0.1 ml tetanus toxoid vaccine on DAYS 0, 14 and 28. Mice in Group 1 (Table 1) received no vaccine. Treatments are done as shown in Table 1. Antibody titers for DAYS 38 are determined by ELISA using tetanus toxoid coated microtiter plates and anti-mouse conjugate. Sera from DAY 30 are assayed by ELISA for interferon-g.

TABLE 1

Group Compound Treatments

| Group | No. Mice | Test Material | ROA | Dose (mg/kg) | Dose Frequency |
|---|---|---|---|---|---|
| 1 | 6 | Vehicle | p.o.* | N/A No vaccine | Days 0, 14, 28 |
| 2 | 6 | Vehicle | p.o. | N/A Vaccinated | Days 0, 14, 28 |
| 3 | 6 | NTR001 | p.o. | 30 | Days 0, 1, 14, |

TABLE 1-continued

Group Compound Treatments

| Group | No. Mice | Test Material | ROA | Dose (mg/kg) | Dose Frequency |
|---|---|---|---|---|---|
| 4 | 6 | NTR001 | p.o. | 60 | 15, 28, 29 Days 0, 14, 28 |
| 5 | 6 | NTR002 | p.o. | 30 | Days 0, 1, 14, 15, 28, 29 |
| 6 | 6 | NTR002 | p.o. | 60 | Days 0, 14, 28 |

*p.o. = oral dose

Figure 3:
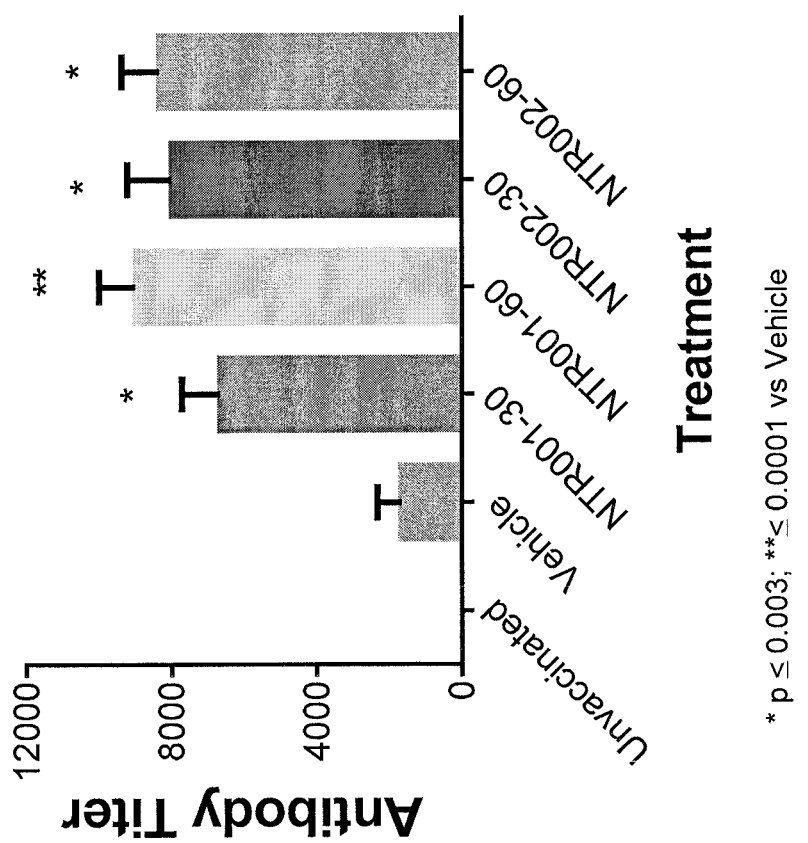
Figure 4:
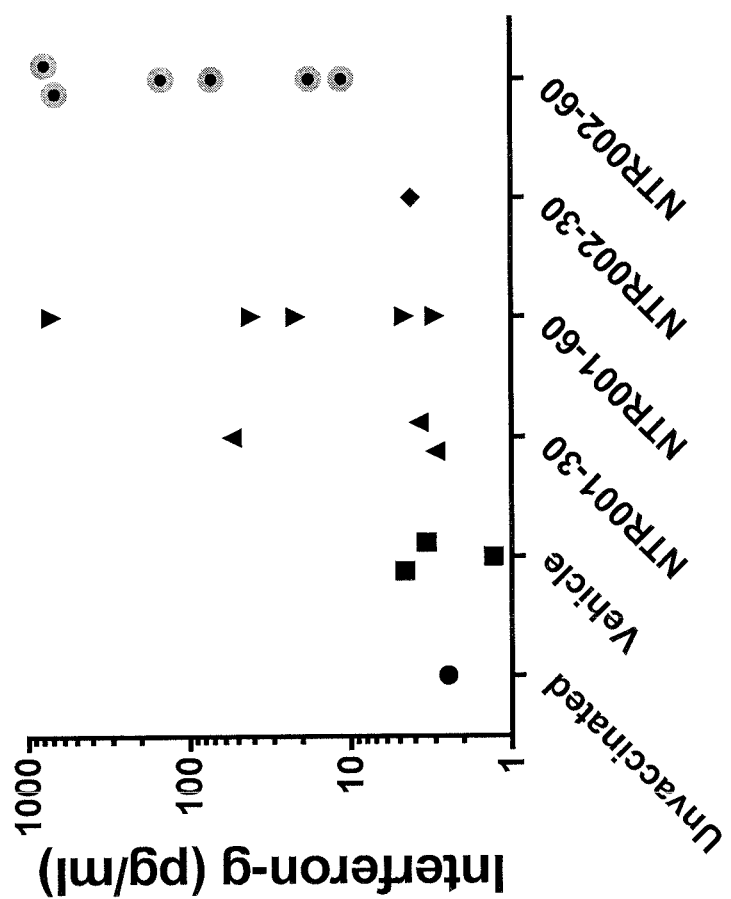
FIG. 4. Serum interferon-g levels on day 30 in vehicle and PNP inhibitors NTR001 and NTR002 treated mice groups in the tetanus toxoid mouse model.

Results: Both NTR001 and NTR002 PNP inhibitors significantly elevated the tetanus toxoid antibody titers compared to the vehicle treated group. The two dosing regimens, 30 mg/kg (given on the day of vaccination and the following day with a total of 6 days of treatment) and 60 mg/kg (given on the day of the vaccination with a total of 3 days of treatment), were effective in increasing the antibody titers (FIG. 3). The interferon-g was elevated in the high dose group (60 mg/kg) for both PNP inhibitors compared to the vehicle treated group (FIG. 4).

Conclusion: PNP inhibitors NTR001 and NTR002 enhance the potency of the tetanus toxoid vaccine by increasing the antibody titers and importantly, the PNP inhibitors induced Th1 responses associated with the induction of interferon-g. Thus, the PNP inhibitors represent a novel approach to enhancing both cellular and humoral immunity and may be useful as a vaccine adjuvant for prevention and treatment of infection and cancer.

EXAMPLE 3

Evaluation of PNPi as Anticancer Agent in Mouse Melanoma Model

Chemotherapy is used to treat diverse cancers, but chemotherapy alone is insufficient to cure many advanced cancers, owing to side effects and the limited efficacy against chemo-resistant or relapsing tumors. The need for establishing more efficacious anticancer strategies led to the development of immunotherapies. This Example demonstrates that PNP demonstrate efficacy in reducing tumor volume and/or increasing survival in a syngeneic mouse model of B16 tumors in C57BL/6 mice.

Method: Cancer cells were injected subcutaneously in right flank of each mouse, $1 \times 10^4$ cells in 0.1 ml PBS with 20% Matrigel. Treatment with the NTR001 was initiated on day 6 after injection of tumor cells. Tumor volume and survival were recorded every 3-4 days. Treatment arms were as follows:

TABLE 2

GROUP TREATMENTS

| Group | No. Mice | Material | Dose (mg/kg) | ROA | Frequency |
|---|---|---|---|---|---|
| 1 | 10 | Vehicle | 0 | PO | 4 wks (week on/off) |
| 2 | 10 | NTR001 | 30 | PO | 4 wks (week on/off) |
| 3 | 10 | Cyclo-phosphamide | 100 | IP | Single dose |
| 4 | 10 | Cyclo-phosphamide NTRPP1 | 100 30 | IP PO | Single dose 4 wks qd/week on/off* |
| 5 | 10 | NTR001 | 5 | Drinking water | 28 days |
| 6 | 10 | Cyclo-phosphamide NTR001 | 100 5 | IP Drinking water | Single Dose 28 days |

*one week on treatment one week off treatment

Figure 5:
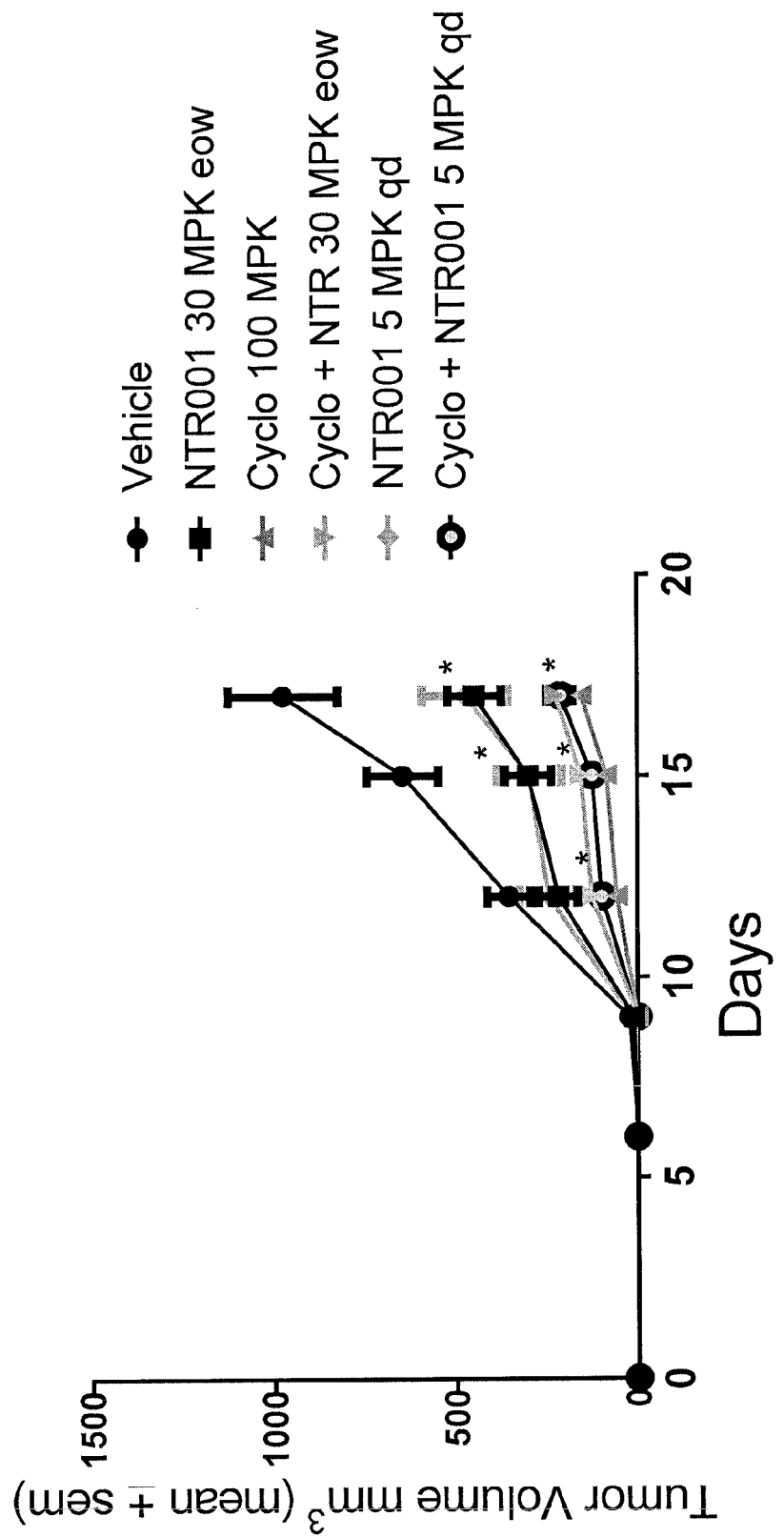
FIG. 5. Effects of PNP inhibitor NTR001 and chemotherapeutic agent cyclophosphamide on tumor volume in the mouse melanoma model.
Figure 6:
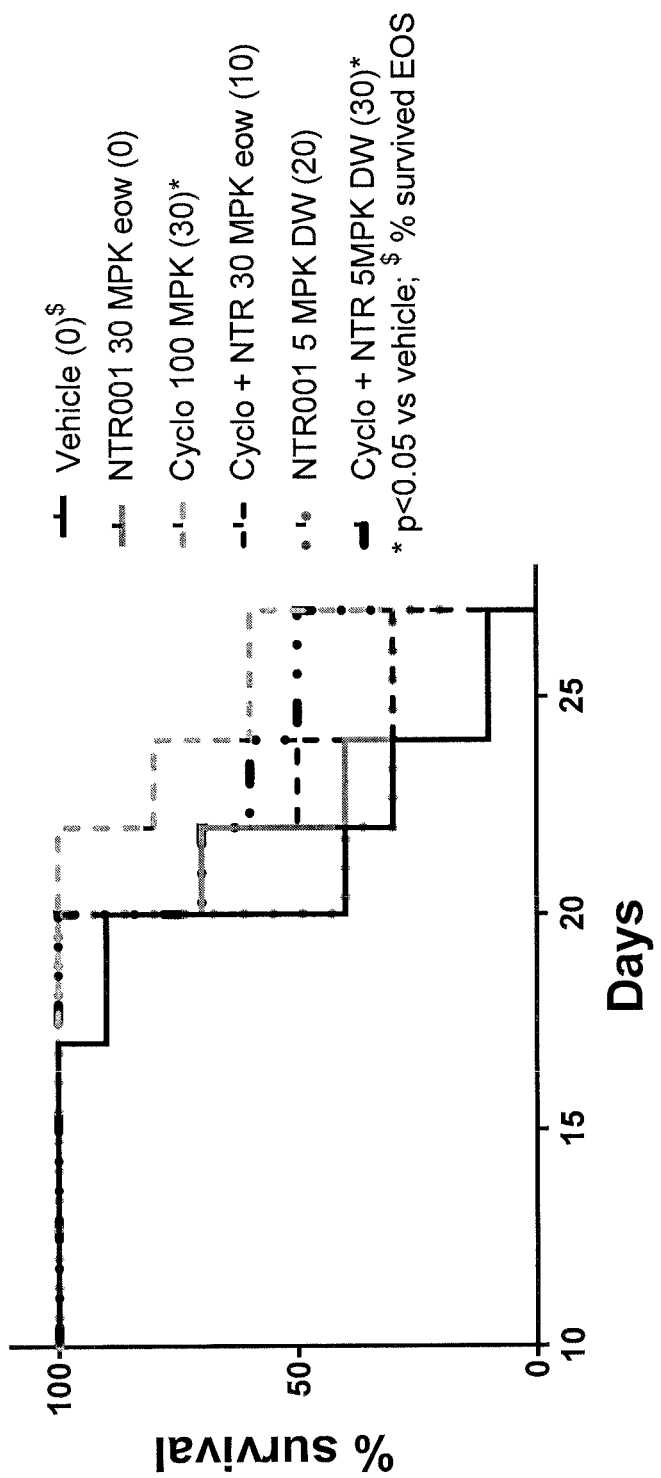
FIG. 6. Effect of PNP inhibitor NTR001 and chemotherapeutic agent cyclophosphamide on survival in the mouse melanoma model.

Results: Treatment with NTR001 resulted in a significant decrease in tumor volume (FIG. 5). Treatment with NTR001 demonstrated 0-20% survival as single agent (FIG. 6). Cyclcophosphamide and combination of cyclophosphamide with NTR001 at 5 mg/kg dose demonstrated 30% survival whereas there were no survivors in the vehicle treated group.

Conclusion: PNP inhibitor NTR001 demonstrated significant efficacy in the syngeneic mouse melanoma model. Combinations of NTR001 with other anticancer angents is also contemplated. Treatment with alternate doses and dose schedule is also warranted.

EXAMPLE 4

Evaluation of Antibacterial Activity of PNPi in Mouse Model of *L. Monocytogenes* Infection In the past, antiviral and antibacterial research has focused mainly on viral and bacterial targets. Due to continued growth of drug resistant organisms the search for effective and differentiated antiviral and antibacterial therapies continues. Development of immune-potentiating agent is one of the strategies being pursued to identify new anti-infective agents. This Example investigates whether PNP inhibitors NTR001 and NTR002 administered by oral and intraperitoneal routes demonstrate antibacterial effect in the mouse model of *Listeria monocytogenes* infection.

Method: Balb/c mice are infected with $1 \times 10^6$ CFU of *L. monocytogenes* (ATCC Strain35152, hemolytic substrain) by intravenous route. The treatment of various groups is initiated −4 hr prior to infection except for Groups 3 and 7 for which treatment was initiated 2 days prior to infection and group 6 and 10 for which treatment was initiated 5 days prior to infection. Weight and survival are the end points of the study. Treatment arms were as follows:

TABLE 3

TREATMENT GROUPS

| Group | # mice | Treatment | Dose (mg/kg) | Route | Frequency |
|---|---|---|---|---|---|
| 1 | 5 | Vehicle | 10 ml/kg | PO | DAYS 0, 1, 2 |
| 2 | 10 | Vehicle | " | PO | DAYS 0, 1, 2 |
| 3 | " | NTR001 | 30 | PO | DAYS −2, −1, 0, 1, 2 |
| 4 | " | " | " | PO | DAYS 0, 1, 2 |
| 5 | " | " | " | IP | DAYS 0, 1, 2 |
| 6 | " | " | 2 | DW | DAY−5 thru end |
| 7 | " | NTR002 | 30 | PO | DAYS −2, −1, 0, 1, 2 |
| 8 | " | " | " | PO | DAYS 0, 1, 2 |
| 9 | " | " | " | IP | DAYS 0, 1, 2 |
| 10 | " | " | 2 | DW | DAY−5 thru end |

PO = oral gavage;
IP = intraperitoneal injection;
DW = drinking water

Figure 7:
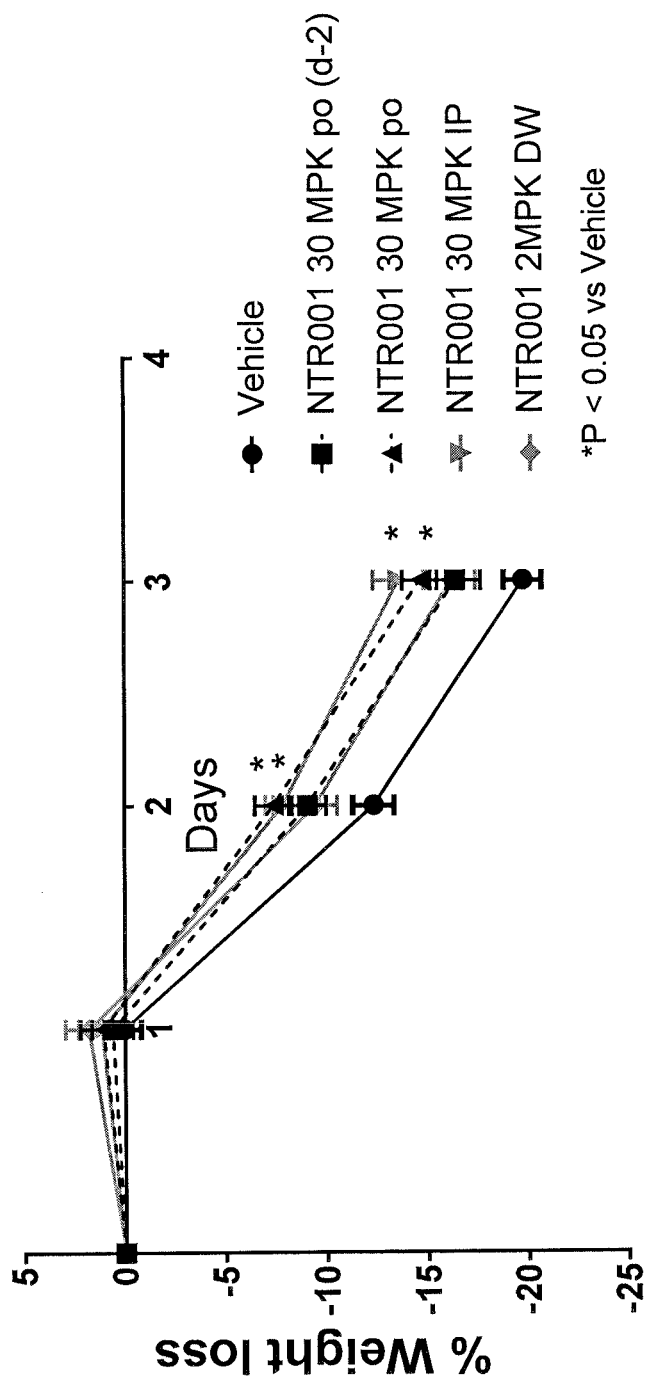
FIG. 7. Effect of PNP inhibitor NTR001 on weight loss in the mouse model of *L. Monocytogenes* infection.
Figure 8:
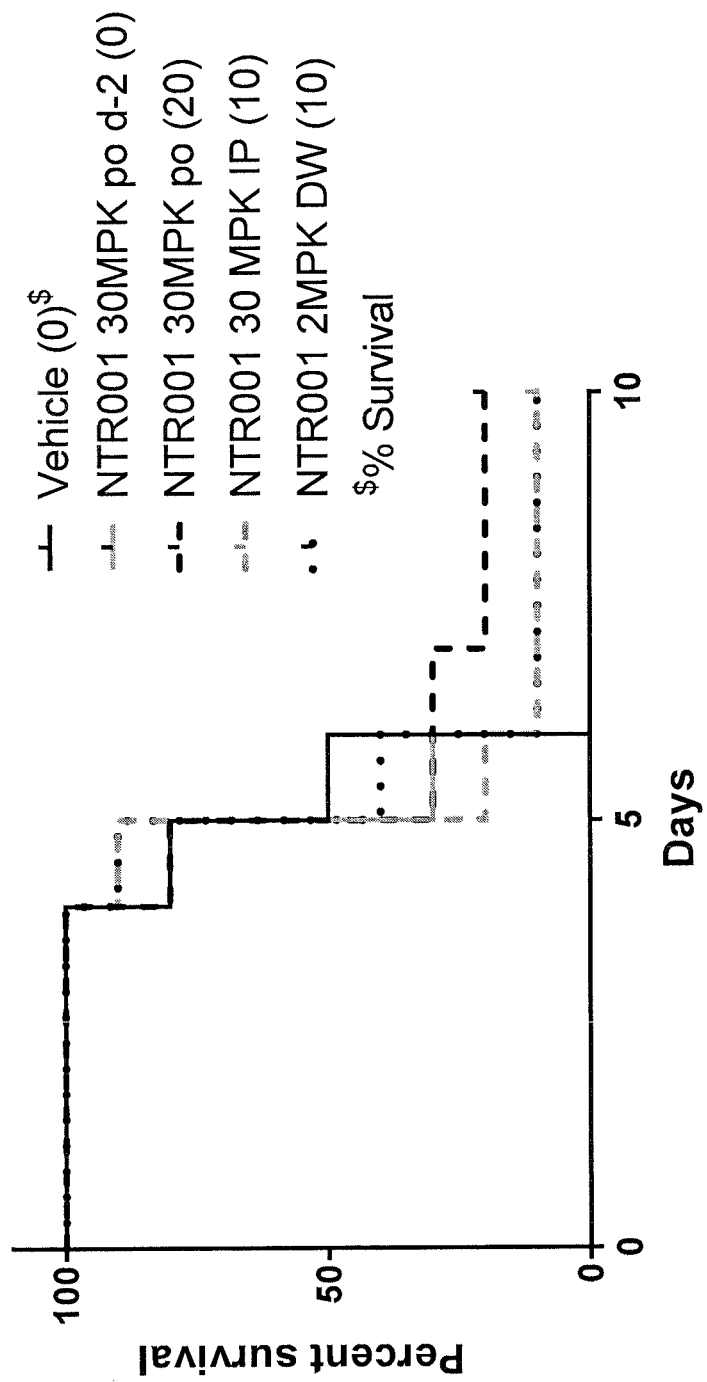
FIG. 8. Effect of PNP inhibitor NTR001 on survival in the mouse model of *L. Monocytogenes* infection.
Figure 9:
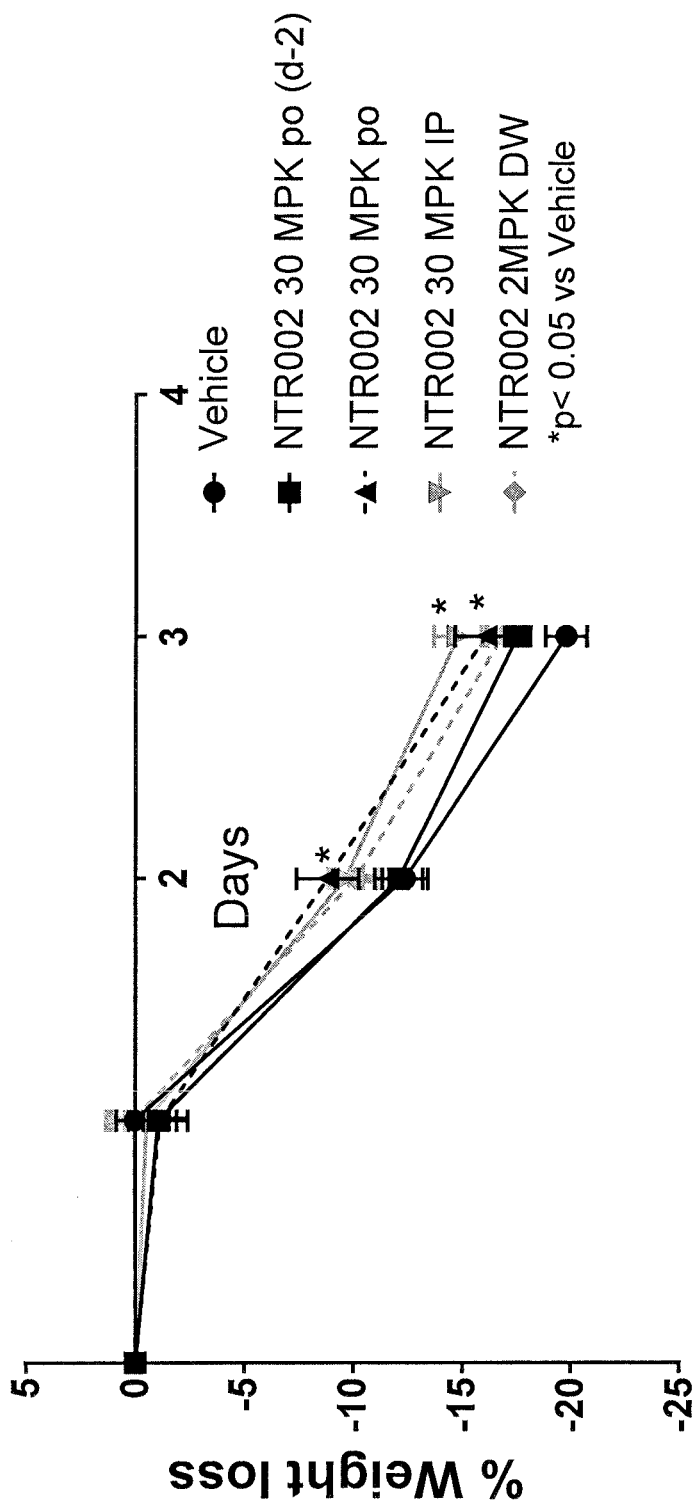
FIG. 9. Effect of PNP inhibitor NTR002 on weight loss in the mouse model of *L. Monocytogenes* infection.
Figure 10:
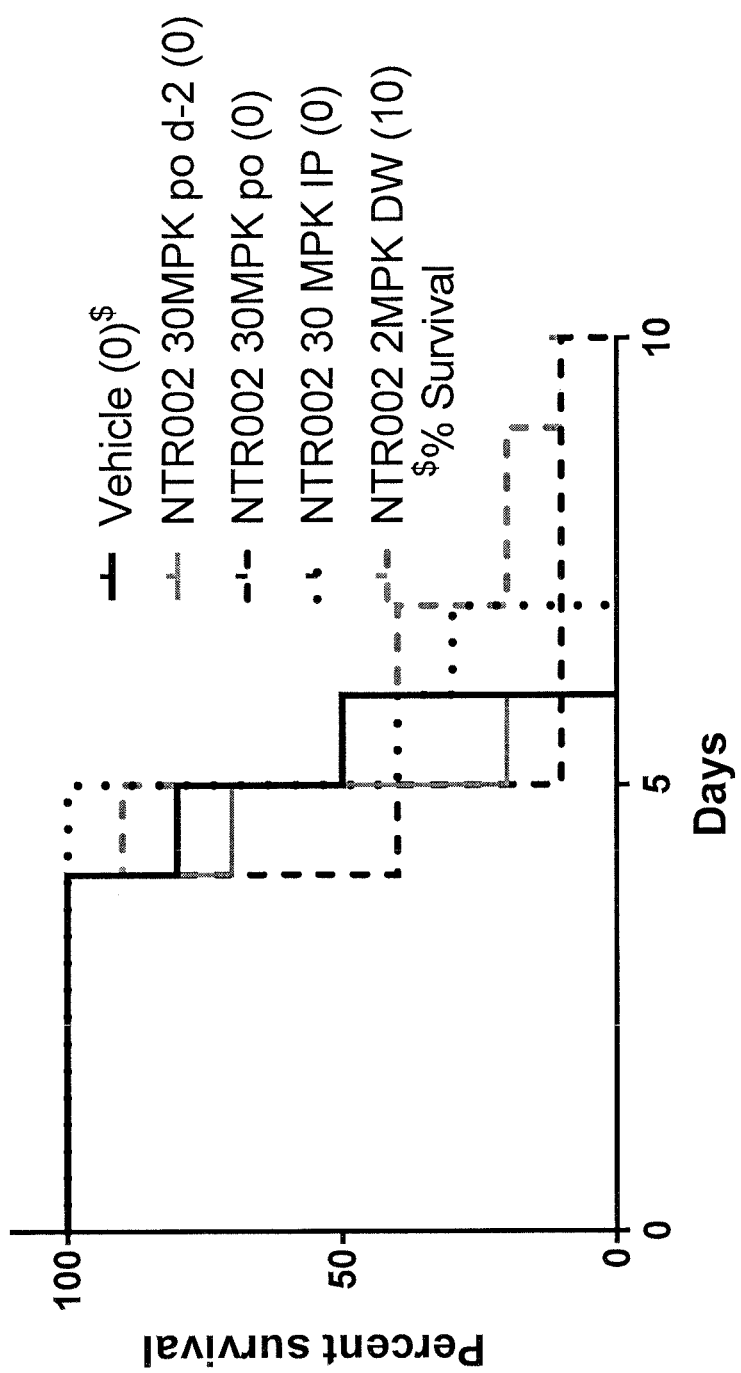
FIG. 10. Effect of PNP inhibitor NTR002 on survival in the mouse model of *L. Monocytogenes* infection.

Results: Treatment with NTR001 and NTR002 resulted in significant decrease in weight loss (FIGS. 7 and 9) and protection of 10-20% of the animals (FIGS. 8 and 10).

Conclusion: PNP inhibitors NTR001 and NTR002 demonstrated significant benefit in mouse model of *L. monocytogenes* infection. Treatment with alternate doses and dose schedule is also warranted.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. It will be appreciated that the invention is in no way dependent upon particular results achieved in any specific example or with any specific embodiment. Articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims or from the description above is introduced into another claim. For example, any claim that is dependent on another claim can be modified to include one or more elements, limitations, clauses, or descriptive terms, found in any other claim that is dependent on the same base claim. Furthermore, where the claims recite a composition, it is to be understood that methods of using the composition for any of the purposes disclosed herein are included within the scope of the invention, unless otherwise indicated or unless it would be evident to one of ordinary skill in the art that a contradiction or inconsistency would arise. Methods can include a step of providing a subject suffering from a targeted disease or condition, or being at risk of developing a disease or condition, a step of diagnosing a subject as having a targeted disease or condition or as being at risk of a disease or condition, and/or a step of selecting a subject for which an inventive composition or method would be suitable.

Where elements are presented as lists, it is to be understood that each subgroup of the elements is also disclosed, and any element(s) can be removed from the group. For purposes of conciseness only some of these embodiments have been specifically recited herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Any particular embodiment, aspect, element, feature, etc., of the present invention, or any combination thereof, may be explicitly excluded from any one or more claims whether or not such exclusion is expressly recited herein. Applicants reserve the right to proviso out of the claims any specific agent or combination thereof, whether or not such agent or combination thereof, is recited herein.

The disclosures of all references cited herein are hereby incorporated into this specification in their entirety.

What is claimed:

1. A method of treating a subject suffering from a non-hematologic malignancy in which it is desirable to enhance an immune system response in the subject, the method comprising administering to the subject an amount of a purine nucleoside phosphorylase (PNP) inhibitor effective to increase an amount of at least one endogenous adjuvant that activates toll-like receptors (TLR's) in the subject, wherein the at least one endogenous adjuvant comprises guanosine, inosine, deoxyinosine, nicotinamide adenine dinucleotide (NAD) and combinations thereof.

2. The method according to claim 1, wherein administering of PNP inhibitor to a human is according to a dose and a dosing schedule that does not significantly impact lymphocytes in the human.

3. The method according to claim 1, wherein the PNP inhibitor comprises a transition state analog of PNP having an in-vitro inhibitory constant Ki value of less than about $5 \times 10^{-6}$ M.

4. The method according to claim 1, wherein the in-vitro inhibitor constant Ki value is less than about $5 \times 10^{-8}$ M.

5. The method according to claim 1, wherein the PNP inhibitor comprises one or more compounds selected from Formula 1 (1,5-dihydro-7-[[(3R,4R)-3-hydroxy-4-(hydroxymethyl)pyrrolidin-1-yl]methyl]-4H-pyrrolo[3,2-d]pyrimidin-4-one), Formula II (7-[(2S,3S,4R,5R)-3,4-dihydroxy-5-(hydroxymethyl)-2-pyrrolidinyl]-1,5-dihydro-4H-pyrrolo[3,2-d]pyrimidin-4-one), and Formula III (7-[[(2R,3S)-1,3,4-trihydroxybutan-2-ylamino]methyl]-3H-pyrrolo[3,2-d]pyrimidin-4-one).

6. The method according to claim 1, wherein "administering" is via an enteral or parenteral or topical route.

7. The method according to claim 1, further comprising administering at least one agent identified as an endogenous adjuvant that activates TLRs simultaneous to or subsequent to administering the PNP inhibitor, wherein the endogenous adjuvant comprises guanosine, inosine, deoxyinosine, or nicotinamide adenine dinucleotide (NAD), and wherein the at least one agent comprises the endogenous adjuvant or a pro-drug thereof.

8. The method according to claim 7, wherein the agent identified as an endogenous adjuvant comprises guanosine or a prodrug thereof.

9. The method according to claim 7, wherein the PNP inhibitor comprises one or more compounds selected from Formula 1 (1,5-dihydro-7-[[(3R,4R)-3-hydroxy-4-(hydroxymethyl)pyrrolidin-1-yl]methyl]-4H-pyrrolo[3,2-d]pyrimidin-4-one), Formula II (7-[(2S,3S,4R,5R)-3,4-dihydroxy-5-(hydroxymethyl)-2-pyrrolidinyl]-1,5-dihydro-4H-pyrrolo[3,2-d]pyrimidin-4-one), and Formula III (7-[[(2R,3S)-1,3,4-trihydroxybutan-2-ylamino]methyl]-3H-pyrrolo[3,2-d]pyrimidin-4-one).

* * * * *